United States Patent
Nyssen et al.

(10) Patent No.: US 6,494,941 B2
(45) Date of Patent: Dec. 17, 2002

(54) ACTIVE-COMPOUND-CONTAINING EMULSIONS

(75) Inventors: Peter-Roger Nyssen, Dormagen (DE); Peter Spetmann, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/968,826

(22) Filed: Oct. 1, 2001

(65) Prior Publication Data

US 2002/0115783 A1 Aug. 22, 2002

(30) Foreign Application Priority Data

Oct. 2, 2000 (DE) .......................... 100 48 797
Aug. 31, 2001 (DE) .......................... 101 42 453

(51) Int. Cl.$^7$ ...................... A01N 43/653; A01N 43/64
(52) U.S. Cl. ...................... 106/18.32; 514/383
(58) Field of Search ................ 106/18.32; 514/383

(56) References Cited

U.S. PATENT DOCUMENTS

| | | | |
|---|---|---|---|
| 5,223,524 A | * 6/1993 | Valcke | 514/383 |
| 5,397,795 A | * 3/1995 | Valcke | 514/383 |
| 5,810,266 A | 9/1998 | Nyssen et al. | 241/5 |
| 6,077,339 A | 6/2000 | Nyssen et al. | 106/31.77 |

FOREIGN PATENT DOCUMENTS

EP    393746    * 10/1990
EP    0 764 695    3/1997

* cited by examiner

*Primary Examiner*—Anthony J. Green
(74) *Attorney, Agent, or Firm*—Joseph C. Gil; Godfried R. Akorli; John E. Mrozinski

(57) ABSTRACT

Emulsions of an aqueous or an aqueous-organic continuous phase and an organic discontinuous phase, the latter containing at least a) a combination of active compounds tebuconazole and propiconazole b) one phenol/styrene polyglycol ether of the formula (I)

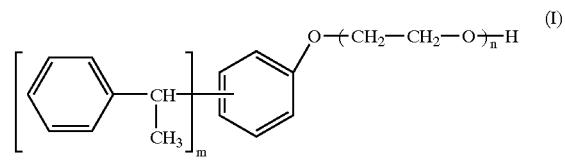

where m=2.7 and n=2 to 13 c) and, if appropriate, an organic solvent which is not miscible with water, wherein the combination of tebuconazole and propiconazole is dissolvable completely at 20° C. in the a phenol/styrene polyglycol ether of the formula (I) or, optionally, together in (i) the phenol/styrene polyglycol ether of the formula (I) and (ii) the organic solvent that is not miscible with water, at a content of more than 0.1% by weight, based on the total weight of the organic phase. Methods for making and using such emulsions.

18 Claims, No Drawings

ACTIVE-COMPOUND-CONTAINING EMULSIONS

BACKGROUND

The invention relates to new emulsions containing the active compound combination tebuconazole and propiconazole, to a process for its preparation and to its use.

It is an aim in different fields, such as for example, crop protection, the protection of materials or the pharmaceutical sector, to prepare storage-stable active compound concentrates which can be introduced into the use medium in dilute form immediately prior to use. However, many active compounds are virtually insoluble in water or only sparingly soluble in preferred organic solvents. However, it becomes an increasing aim to employ aqueous active compound concentrates or active compound concentrates which can be diluted in aqueous media, such as, for example, active compound formulations in the form of suspension concentrates (SC) or emulsion concentrates (EC). In ECs, the active compounds are generally fully dissolved in one or more organic solvents which are emulsifiable in water in conjunction with emulsifiers. As regards the stability of the emulsion and also in particular as regards the undesired precipitation of the active compound as crystalline solid in aqueous dilutions, there is still room for improvement of the known EC formulations. This also applies with regard to increasing the active compound contents and to the use of biodegradable or well-tolerated solvents.

While higher active compound concentrations can be achieved with SCs, in particular aqueous SCs, however, the only disadvantage is frequently the lack of biological activity. Even when the active compounds with medium particle sizes are ground ultrafinely in an order of magnitude of less than a micron, the desired biological activity is still not achieved.

Tebuconazole and propiconazole are valuable biocidal active compounds which, however, cannot be converted in the desired fashion into emulsions with a high active compound content. In particular in a specific field of the protection of materials, namely the protection of timber, attempts to prepare emulsions which are sufficiently stable upon dilution and, when applied by customary impregnation methods, are capable of delivering the active compound(s) sufficiently deep into the wood have remained unsuccessful as yet.

It was therefore the object of the present invention to provide a formulation system for the active compound combination of tebuconazole and propiconazole in the form of active-compound-containing emulsions, in particular microemulsions, which formulation system overcomes the above-described shortcomings.

A further object is to provide emulsion concentrates with high contents of the active compound combination tebuconazole/propiconazole with well tolerated components as base, which emulsion concentrates are sufficiently stable with regard to flocculation, sedimentation or creaming and with regard to crystallization or precipitation of solids (active compound crystals) down to the high dilutions which are desired for use and which are distinguished by a high depth of penetration into timber, in particular green timber, in immersion, coating or pressure-vessel impregnation methods.

SUMMARY

The invention relates to an emulsion comprising (i) an aqueous or an aqueous-organic continuous phase and (ii) an organic discontinuous phase containing at least a) a combination of of tebuconazole and propiconazole,
b) a phenol/styrene polyglycol ether of the formula (I)

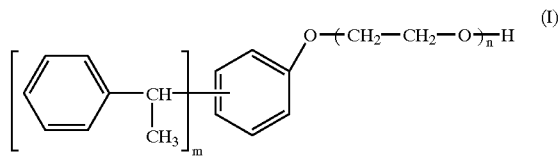

wherein m is 2.7 and n is 2 to 13; and c) optionally, an organic solvent that is not miscible with water, wherein the component selected from the group consisting of tebuconazole and propiconazole is dissolvable completely at 20° C. in the a phenol/styrene polyglycol ether of the formula (I) or, optionally, together in (i) the phenol/styrene polyglycol ether of the formula (I) and (ii) the organic solvent that is not miscible with water, at a content of more than 0.1% by weight, based on the total weight of the organic phase.

In one embodiment, the invention also relates to a method for making such an emulsion. In another embodiment, the invention relates to a method for protecting timber or a timber material from attack by wood-destroying or wood-discoloring micro-organisms comprising treating the timber or the timber material with such an emulsion.

DESCRIPTION

The present invention therefore relates to emulsions of an aqueous or an aqueous-organic continuous phase and an organic discontinuous phase, the latter containing at least a) one combination of the active compounds tebuconazole and propiconazole
b) one phenol/styrene polyglycol ether of the formula (I)

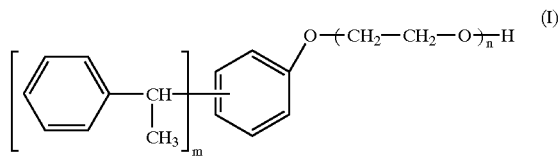

where m=2.7 and n=2 to 13, preferably 2 to 10, c) and, if appropriate, an organic solvent which is not miscible with water, characterized in that component a) is dissolved completely in b) or, if appropriate in b) and c) together with a content of more than 0.1% by weight, in particular >1% by weight, especially preferably >10% by weight, at 20° C. based on the total weight of the organic phase.

The active compound tebuconazole is known under the tradename FOLICUR® (Bayer AG). Likewise, the active compound propiconazole is known under the tradename WOCOSEN® Technical (Janssen).

If appropriate, the emulsions according to the invention contain further biologically active compounds a), for example from the group of the pharmaceutical active compounds and the crop protection agents, in particular biocides, microbicides, pesticides, such as fungicides, bactericides, virucides, herbicides, insecticides, acaricides, nematicides, plant growth regulators and bird repellents, and also disinfectants.

If appropriate, the emulsions according to the invention can contain, as component b), further organic compounds from the group of the reaction products of alkylene oxides with compounds capable of being alkylated, such as, for example, fatty alcohols, fatty amines, fatty acids, phenols, alkylphenols, carboximides and resinic acids, preferably balsamic resin and/or abietic acid.

If appropriate, the emulsions according to the invention can contain, as component c), further organic solvents which are not miscible with water, for example from the group of the aliphatic, cycloaliphatic or aromatic hydrocarbons or the acetate-type solvents.

Suitable as organic solvents (c) are, preferably, natural, fully- or semisynthetic compounds and, if appropriate, mixtures of these solvents which are fully miscible or soluble with the compounds (b) in the temperature range of from 20 to 130° C. Preferably suitable solvents are those from the group of the aliphatic, cycloaliphatic or aromatic hydrocarbons which are liquid at room temperature, in particular

- oils, such as, for example, mineral oils, paraffins, isoparaffins, fully-synthetic oils such as silicon oils, semisynthetic oils based on, for example, glycerides of unsaturated fatty acids of medium chain length, essential oils,
- esters of natural or synthetic, saturated or unsaturated fatty acids, preferably $C_8$–$C_{22}$-fatty acids, in particular $C_8$–$C_{18}$-fatty acids, especially preferably methyl esters of rapeseed oil or 2-ethylhexyl laurate,
- alkylated aromatics and their mixtures,
- alkylated alcohols, in particular fatty alcohols,
- linear, primary alcohols obtained by hydroformylation,
- terpene hydrocarbons and
- naphtene-type oils, such as, for example, Enerthene.

Further preferred solvents of component c) are those from the group of the acetate-type solvents such as, for example, 1,2-propanediol diacetate, 3-methyl-3-methoxybutyl acetate, ethyl acetate and the like. The solvents can be employed individually or as mixtures with each other.

In addition to components a) to c), the organic discontinuous phase of the emulsions according to the invention may additionally contain further additives which have a solubility of <0.1 g/l, in water, but a solubility of >10 g/l in comp. b) and/or c).

In a preferred composition, the organic discontinuous phase of the emulsions according to the invention contains
a) 0.5 to 40% by weight, in particular 1 to 20% by weight, of propiconazole and tebuconazole,
b) 20 to 99.5% by weight, in particular 40 to 99% by weight, of compound (I),
c) 1 to 80% by weight of an organic solvent which is not miscible with water, in particular 1,2-propanediol diacetate, based on the total discontinuous phase.

The continuous aqueous or aqueous-organic phase (=carrier phase of the emulsion droplets) of the active-compound-containing emulsions or microemulsions according to the invention preferably contains
d) water,
e) if appropriate, organic solvent,
f) at least one natural or synthetic surface-active agent which has a solubility of >10 g/l, in particular >100 g/l in water (d) at 20° C., and, if appropriate, further adjuvants.

Preferred organic solvents of component (e) are solvents which are soluble or miscible in water, in particular with a solubility in water of >5.0 g/l at 20° C., in particular >15 g/l.

Examples of suitable organic solvents are: aliphatic $C_1$–$C_4$-alcohols such as methanol, ethanol, isopropanol, n-propanol, n-butanol, isobutanol or tert-butanol, aliphatic ketones such as acetone, methyl ethyl ketone, methyl isobutyl ketone or diacetone alcohol, polyols, such as ethylene glycol, propylene glycol, butylene glycol, 1,4-butanediol, 1,5-pentanediol, 1,6-hexanediol, diethylene glycol, triethylene glycol, trimethylolpropane, polyethylene glycol or polypropylene glycol with a mean gram-molecular weight of 100 to 4000 g/mol, preferably 200 to 1500 g/mol, or glycerol, monohydroxyethers, preferably monohydroxyalkyl ethers, especially preferably mono-$C_1$–$C_4$-alkyl glycol ethers such as ethylene glycol monoethyl ether, ethylene glycol monomethyl ether, diethylene glycol monomethyl ether or diethylene glycolmonoethyl ether, diethylene glycol monobutyl ether, dipropylene glycol monoethyl ether, thiodiglycol, triethylene glycol monomethyl ether or triethylene glycol monoethyl ether, furthermore 2-pyrrolidone, N-methyl-2-pyrrolidone, N-ethyl-pyrrolidone, N-vinylpyrrolidone, 1,3-dimethylimidazolidone, dimethylacetamide and dimethyl formamide.

Mixtures of solvents, for example those mentioned herein, are also suitable. The amount of the solvents (e) employed in the aqueous continuous phase is in general less than 60% by weight, preferably less than 40% by weight, based on the continuous phase.

Surface-active agents (f) are understood as meaning emulsifiers, wetters, dispersants, antifoams or solubilizers which are soluble, preferably fully soluble, in the aqueous phase. In particular, they can be nonionic, anionic, cationic or amphoteric or of monomeric, oligomeric or polymeric nature. The choice of the surface-active agents (f) is not limited in accordance with the invention and must be matched with the discontinuous phase to be stabilized with regard to the desired type of emulsion (for example miniemulsion or microemulsion) and the stability of the emulsion, in particular the sedimentation and/or creaming of the disperse phase.

Preferred surface-active agents of component (f) which must be mentioned are those of f1) to f9):
f1) Alkoxylation product which can be obtained by ethylene-oxide-alkoxylation or propylene-oxide-alkoxylation of condensates of phenolic OH-containing aromatics with formaldehyde and NH functional groups.
f2) Inorganic salts which are soluble in water, in particular borates, carbonates, silicates, sulfates, sulfites, selenates, chlorides, fluorides, phosphates, nitrates and aluminates of the alkali metals and alkaline earth metals and other metals and also ammonium;
f3) Polymers composed of recurrent succinyl units, in particular polyaspartic acid.
f4) Nonionic or ionically modified compounds form the group of the alkoxylates, alkylolamides, esters, amine oxides and alkyl polyglycosides, in particular reaction products of alkylene oxides with compounds capable of being alkylated, such as, for example, fatty alcohols, fatty amines, fatty acids, phenols, alkyl phenols, carboximides and resinic acids.

These are, for example, ethylene oxide adducts from a class of the reaction products of ethylene oxide with:
m) saturated and/or unsaturated fatty alcohols with 6 to 25 C atoms or
n) alkyl phenols with 4 to 12 C atoms in the alkyl radical or
o) saturated and/or unsaturated fatty amines with 14 to 20 C atoms or
p) saturated and/or unsaturated fatty acids with 14 to 22 C atoms or
q) hydrogenated and/or unhydrogenated resinic acids, r) esterification and/or arylation products prepared from natural or modified, optionally hydrogenated castor oil lipid bodies which, if appropriate, are linked by esterification with dicarboxylic acids to give recurrent structural units.

f5) Ionic or nonionic compounds from the group of the reaction products of alkylene oxide with sorbitan ester [Tween®, ICI], oxalkylated acetylene diols and acetylene glycols, oxalkylated phenols, in particular phenol/styrene polyglycol ethers of formula I) and II) with the difference that n is a number from 14 to 120, and ionically modified phenol/styrene polyglycol ethers of the formula I) or II) as disclosed for example in EP-A 839 879 [or EP-A-764 695]. The term "ionic modification" is understood as meaning, for example, sulfation, carboxylation or phosphatation. Ionically modified compounds can be present either in the form of their free acids or, preferably, as salts, in particular as alkali metal or amine salt, preferably diethylamine salt.

f6) Ionic or nonionic polymeric surface-active agents from the group of the homo- and copolymers, graft and graft copolymers and random and linear block copolymers. Examples of suitable polymeric surface-active agents (f6) are polyethylene oxides, polypropylene oxides, polyoxymethylenes, polytrimethylene oxides, polyvinyl methyl ethers, polyethylene imines, polyacrylic acid, polyaryl amides, polymethacrylic acids, polymethacrylamides, poly-N,N-dimethyl-acrylamides, poly-N-isopropyl acrylamides, poly-N-acrylglycinamides, poly-N-methacryl-glycinamides, polyvinyloxazolidones, polyvinylmethyloxazolidones.

f7) Anionic surface-active agents such as, for example, alkyl sulfates, ether sulfates, ether carboxylates, phosphate esters, sulfosuccinate amides, paraffin sulfonates, olefin sulfonates, sarcosinates, isothionates and taurates.

f8) Anionic surface-active agents from the group of what is known as dispersants, in particular condensates which can be obtained by reacting naphthols with alkanols, subjecting alkylene oxide to an addition reaction and at least partially converting the terminal hydroxyl groups into sulfo groups or monoesters of maleic acid, phthalic acid or succinic acid, sulfosuccinic esters, alkylbenzene sulfonates, and salts of the polyacrylic acids, polyethylene sulfonic acids, polystyrene sulfonic acid, polymethacrylic acids, polyphosphoric acids.

f9) Lignin-type compounds, especially lignosulfonates, for example those which have been obtained by the sulfite or Kraft method. They are preferably products which are partially hydrolyzed, oxidized, propoxylated, sulfonated, sulfomethylated or bisulfonated and which are fractionated by known methods, for example according to the molecular weight or the degree of sulfonation. Mixtures of sulfite and Kraft lignosulfonates are also very effective. Especially suitable are lignosulfonates with a mean molecular weight of greater than 1,000 to 100,000, a content of active lignosulfonate of at least 80% and, preferably, a low content of polyvalent cations. The degree of sulfonation can be varied within wide limits.

In a particularly preferred embodiment, the continuous aqueous phase can also contain, in addition to the abovementioned surface-active agent f), in particular f1) to f9), water-soluble block or block copolymers of component g); they are preferably water-soluble block and block copolymers based on ethylene oxide and/or propylene oxide [Pluronic®, BASF] and/or water-soluble block and block copolymers of ethylene oxide and/or propylene oxide on bifunctional amines [Tetronic®, BASF].

Block copolymers based on polystyrene and polyalkylene oxide, poly(meth)acrylates and polyalkylene oxide and also poly(meth)acrylates and poly(meth)acrylic acids are also suitable.

In addition, the continuous aqueous phase can also contain further customary adjuvants such as, for example, water-soluble wetters, antifoams and/or preservatives.

The emulsions according to the invention preferably contain 1 to 40% by weight, in particular 2 to 20% by weight, of the discontinuous organic phase and 60 to 99% by weight of the continuous aqueous or aqueous-organic phase based on the total emulsion.

Preferred compositions of the emulsions contain 0 to 2000% by weight, in particular 10 to 1000% by weight, of one or more water-soluble surface-active agents of component (f), 0 to 100% by weight, in particular 1 to 50% by weight, of one or more water-soluble block copolymers of component (g) and 0 to 600% by weight, in particular 20 to 400% by weight, of one or more water-soluble organic solvents of component (e), based on the discontinuous organic phase, and also, if appropriate, further customary adjuvants.

If the emulsions are present as microemulsions, they preferably comprise 10 to 2000% by weight, in particular 100 to 1000% by weight, of one or more water-soluble surface-active agents of component (f), 0 to 100% by weight, in particular 1 to 50% by weight, of one or more water-soluble block copolymers of component (g) and 0 to 600% by weight, in particular 20 to 400% by weight, of one or more water-soluble organic solvents of component (e), based on the discontinuous organic phase, and also, if appropriate, further customary adjuvants.

Preferred emulsion types which may be mentioned are:
Macroemulsion: contains droplets >2 µm (microscopic)
Miniemulsion: droplet diameter 0.1 to 2 µm, turbid
Microemulsion: droplet diameter <0.1 µm; transparent Microemulsions are particularly preferred in this context.

Surprisingly, the invention has succeeded in maintaining particularly high contents of active compounds in the discontinuous phase—that is to say, the emulsion droplets—stably in solution at normal temperature (20° C.). In particular in the case of microemulsions (i.e. clear emulsions), considerably higher contents of active compounds (a) were achieved than was expected on the basis of the limit of solubility of the sheer active compounds (a) in the organic compounds (b) and, if appropriate solvent (c), determined at normal temperature (20° C.).

The invention therefore also comprises a method of preparing the active-compound-containing emulsions according to the invention, for example the macroemulsions or microemulsions, wherein the active compound (a) in question is dissolved fully in the organic compound (b), if appropriate with concomitant use of the solvent (c), at a temperature of from 20 to 200° C., if applicable the solution is filtered while hot in the abovementioned temperature range, and the resulting solution is emulsified into the aqueous or aqueous-organic phase, naturally while maintaining the temperature required for complete solubility of the active compound, and the resulting emulsion, for example macro- or microemulsion, is cooled to at temperature of from 10 to 70° C., preferably below 60° C., and, if appropriate, subsequently filtered.

The method can also be carried out in the form of what is known as reversal emulsion, wherein some of the aqueous or aqueous-organic phase is first introduced into, and emulsified in, the active-compound-containing (oil) phase (type W/O emulsion) and the product is subsequently converted into the desired emulsion (Type O/W emulsion) by successively adding the remainder of the aqueous phase.

For the dispersing (emulsifying) process, methods such as stirring, dissolver emulsifying, emulsifying by means of rotor-stator apparatuses, Ultraturrax, high-pressure homogenizer, jet dispersion and sonication are suitable. The choice of method depends on the desired fine distribution of the discontinuous phase (macromeulsion, miniemulsion or microemulsion).

The methods can be applied batchwise or else in continuous form; in general, a continuous procedure is preferred since this allows the two phases to be mixed and emulsified intensely in a small space, if appropriate under pressure and with the application of shear forces, and subsequently to be cooled in the shortest possible time to the temperature necessary for stabilizing the emulsion (with regard to precipitation of the active compound from the discontinuous phase (or from the organic compound b)). Especially preferred is a continuous procedure for achieving microemulsions or miniemulsions with a maximum droplet size of the discontinuous phase of <1 $\mu$m, in particular <0.5 $\mu$m, very especially <0.1 $\mu$m. In general, the two phases are first prepared separately, for example by dissolving and stirring the components, if appropriate while raising the temperature, and subsequently feeding them continuously to an emulsifying device.

Preferred methods are those in which emulsification is effected with high energy input, for example sonification, high-pressure homogenization or jet dispersion at pressures of from 2 to 2500 bar, in particular 20 to 1000 bar, in one or more passes. The jet-dispersion method, which is especially preferred, and devices suitable therefor are illustrated for example in DE-A 19536 845. In particular, this method, combined with suitable temperature control, allows microemulsions to be obtained which have particularly good long-term stability and very high active compound content and which can be applied as stated below.

The final standardization for the desired properties such as viscosity, flow characteristics and preservation can be effected either before, during or after the emulsification process by adding water or further additives.

The emulsions according to the invention are outstandingly suitable for the protection of timber or timber materials from attack by wood-destroying or wood-discolouring micro-organisms.

For use in the protection of timber, the emulsions according to the invention are dispersed finely into water or water-based, optionally binder-containing carrier solutions or dispersions by means of the abovementioned methods. The active-compound-containing emulsions according to the invention are distinguished by high chemical stability (for example stability to hydrolysis) and physical stability in conjunction with a fine distribution which is very good for the performance of the active compound, and are therefore far superior to purely aqueous formulations of the active compounds. Moreover, the active compounds penetrate the timber deeply and permanently. Particularly preferred in this context is the use of the active-compound-containing emulsions for the fungicidal finishing of timber, in particular green timber, and for impregnation. In this context, emulsions according to the invention which are in the form of concentrates are diluted in water to a desired concentration, and these dilutions are applied to timber by means of dipping, coating or pressure-vessel impregnation methods, where in particular emulsions according to the invention in the form of microemulsions are distinguished by good active compound penetration and good long-term stability of the active compound.

The invention is further described in the following illustrative examples in which all parts and percentages are by weight unless otherwise indicated.

EXAMPLES

Example 1

To prepare the discontinuous organic phase, a) 14% by weight of tebuconazole and 15% by weight of propiconazole were dissolved fully at room temperature in b) 44% by weight of 1,2-propanediol diacetate, and c) 27% by weight of phenol/styrene polyglycol ether of the formula (I) where m=2.7 and n=10 were subsequently added.

The resulting oil phase was subsequently introduced into the aqueous-organic continuous phases consisting of 99.10% by weight of deionized water and 0.10% by weight of silicone-based antifoam at room temperature by means of a high-speed stirrer and dispersed for approximately 0.5 minute.

This gave an emulsion with the following characteristics.

| Emulsion | Type | Macroemulsion |
|---|---|---|
| | Discontinuous phase | 2.00% |
| | Continuous phase | 98.00% |
| Assessment of the emulsion | Initial consistency | Milky Fluid |
| After 1 week at RT | Microscopic droplet size | >10 $\mu$m |
| After 1 week at RT | Microscopic crystals | No |
| After 1 week at RT | Separation of the emulsion | Flocculation |
| After 1 week at RT | Crystalline sediment | No |
| After 2 weeks at RT | Crystalline sediment | No |
| Assessment of the discontinuous oil phase | Viscosity | Clear, fluid |
| After 1 week at RT | Recrystallization | No |

Example 2

To prepare the discontinuous phase, the procedure of Example 1 was followed.

The resulting oil phase was subsequently introduced into the aqueous-organic continuous phases consisting of 85.0% by weight of deionized water, 7.40% by weight of Emulgator® KS (=alkoxylated castor oil lipid body, Bayer AG) 7.40% by weight of dispersant VPSP 25031 (ionically modified phenol/styrene polyglycol ether in accordance with Ex. 10 of WO-A 9937718) and 0.20% by weight of silicone-based antifoam by means of a high-speed stirrer while maintaining the temperature and dispersed for approximately 0.5 minute.

This gave an emulsion with the following characteristics

| Emulsion | Type | Microemulsion |
|---|---|---|
| | Discontinuous phase | 1.00% |
| | Continuous phase | 99.00% |
| Assessment of the emulsion | Initial consistency | Clear fluid |
| After 1 week at RT | Microscopic droplet size | Not determined |
| After 1 week at RT | Microscopic crystals | No |
| After 1 Week at RT | Separation of the emulsion | No |
| After 1 week at RT | Crystalline sediment | No |
| After 2 weeks at RT | Crystalline sediment | No |

| Emulsion | Type | Microemulsion |
|---|---|---|
| Assessment of the discontinuous oil phase After 1 week at RT | Viscosity Recrystallization | Clear, fluid No |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An emulsion comprising:
   an aqueous or an aqueous-organic continuous phase; and
   an organic discontinuous phase comprising
      a component comprising a combination of tebuconazole and propiconazole,
      a phenol/styrene polyglycol ether of the formula (I)

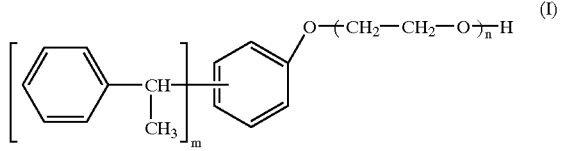

wherein m is 2.7 and n is 2 to 13, and
      optionally, an organic solvent which is not miscible with water, wherein the component is completely dissolved at 20° C. in the phenol/styrene polyglycol ether of the formula (I) or, optionally, is dissolved in the phenol/styrene polyglycol ether of the formula (I) and the organic solvent that is not miscible with water, at a content of more than 0.1% by weight, based on the total weight of the organic discontinuous phase.

2. The emulsion of claim 1, wherein for the phenol/styrene polyglycol ether of the formula (I), n is 10 and wherein the organic solvent which is not miscible with water is 1,2-propanediol diacetate.

3. The emulsion of claim 1, wherein the emulsion contains, based on the total emulsion, from 1 to 40% by weight, of the organic discontinuous phase and from 60 to 99% by weight of the aqueous or aqueous-organic continuous phase.

4. The emulsion of claim 1, wherein the aqueous or aqueous-organic continuous phase further includes
   water,
   optionally, an organic solvent,
   optionally, at least one natural or synthetic surface-active agent which has a solubility of >10 g/l, in water at 20° C.

5. The emulsion of claim 1, wherein the emulsion contains, based on the organic discontinuous phase,
   from 0 to 600% by weight of one or more organic solvents which are soluble in water,
   from 0 to 2000% by weight, of one or more surface-active agents which are soluble in water and
   from 0 to 100% by weight, of one or more block or block copolymers which are soluble in water.

6. The emulsion of claim 1, wherein the emulsion contains, based on the organic discontinuous phase,
   from 0.5 to 40% by weight of a mixture of propiconazole and tebuconazole,
   from 20 to 99.5% by weight of the compound of the formula (I) where n is 10, and
   from 1 to 80% by weight of 1,2-propanediol diacetate.

7. The emulsion of claim 1, wherein the emulsion is a microemulsion.

8. The emulsion of claim 7, wherein the microemulsion contains, based on the organic discontinuous phase,
   from 0 to 600% by weight, of one or more organic solvents which are soluble in water,
   from 10 to 2000% by weight, of one or more surface-active agents which are soluble in water, and
   from 0 to 100% by weight, of one or more block or block copolymers which are soluble in water.

9. The emulsion of claim 1, wherein the component of the organic discontinuous phase consists essentially of tebuconazole and propiconazole.

10. The emulsion of claim 1, wherein the component of the organic discontinuous phase consists of tebuconazole and propiconazole.

11. A method of preparing an emulsion comprising an aqueous or an aqueous-organic continuous phase and an organic discontinuous phase comprising a component comprising a combination of tebuconazole and propiconazole, a phenol/styrene polyglycol ether of the formula (I)

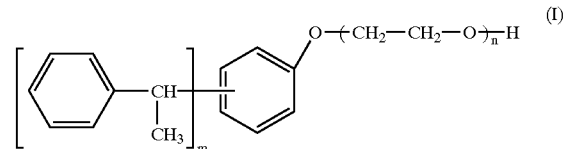

wherein m is 2.7 and n is 2 to 13; and optionally, an organic solvent which is not miscible with water, wherein the combination of tebuconazole and propiconazole is completely dissolved at 20° C. in the a phenol/styrene polyglycol ether of the formula (I) or, optionally, is dissolved in the phenol/styrene polyglycol ether of the formula (I) and the organic solvent which is not miscible with water, at a content of more than 0.1% by weight, based on the total weight of the organic discontinuous phase, the method comprising
      forming a solution by dissolving fully the combination of tebuconazole and propiconazole in the phenol/styrene polyglycol ether of the formula (I) with concomitant use of the solvent which is not miscible in water at a temperature of from 20 to 200° C.,
      optionally filtering the solution while hot in the temperature range stated,
      emulsifying the solution into the aqueous or aqueous-organic continuous phase to form an emulsion,
      cooling the emulsion to a temperature of from 10 to 70° C., and,
      optionally filtering the emulsion.

12. The method of claim 11, wherein the component of the organic discontinuous phase consists essentially of tebuconazole and propiconazole.

13. The method of claim 11, wherein the component of the organic discontinuous phase consists of tebuconazole and propiconazole.

14. The method of claim 11, wherein the component is dissolved with a content of more than >1% by weight, at 20° C. based on the total weight of the organic discontinuous phase.

15. A method for protecting timber or a timber material from attack by wood-destroying or wood-discoloring microorganisms comprising treating the timber or the timber material with an emulsion comprising an aqueous or an aqueous-organic continuous phase and an organic discontinuous phase comprising a component comprising a combination of tebuconazole and propiconazole, a phenol/styrene polyglycol ether of the formula (I)

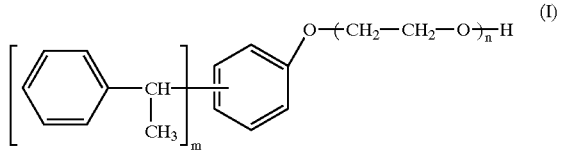

wherein m is 2.7 and n is 2 to 13; and optionally, an organic solvent which is not miscible with water, wherein the combination of tebuconazole and propiconazole is completely dissolved at 20° C. in the phenol/styrene polyglycol ether of the formula (I) or, optionally, is dissolved in the phenol/styrene polyglycol ether of the formula (I) and the organic solvent which is not miscible with water, at a content of more than 0.1% by weight, based on the total weight of the organic discontinuous phase.

16. The method of claim 15, wherein the component of the organic discontinuous phase consists essentially of tebuconazole and propiconazole.

17. The method of claim 15, wherein the component of the organic discontinuous phase consists of tebuconazole and propiconazole.

18. The method of claim 15, wherein the component is dissolved with a content of more than 10% by weight, at 20° C. based on the total weight of the organic discontinuous phase.

* * * * *